United States Patent
Zatta

(10) Patent No.: US 11,490,932 B2
(45) Date of Patent: Nov. 8, 2022

(54) POLYAXIAL PEDICLE SCREW SYSTEM

(71) Applicant: Next Orthosurgical, Inc., Vista, CA (US)

(72) Inventor: Daniel Zatta, Vista, CA (US)

(73) Assignee: Next Orthosurgical, Inc., Vista, CA (US)

( * ) Notice: Subject to any disclaimer, the term of this patent is extended or adjusted under 35 U.S.C. 154(b) by 0 days.

(21) Appl. No.: 16/178,112

(22) Filed: Nov. 1, 2018

(65) Prior Publication Data

US 2020/0138483 A1 May 7, 2020

(51) Int. Cl.
*A61B 17/70* (2006.01)
*A61B 17/00* (2006.01)

(52) U.S. Cl.
CPC ...... *A61B 17/7035* (2013.01); *A61B 17/7032* (2013.01); *A61B 2017/00526* (2013.01)

(58) Field of Classification Search
CPC .................. A61B 17/7035; A61B 2017/00526
USPC ................................ 606/250–279, 300–330
See application file for complete search history.

(56) References Cited

U.S. PATENT DOCUMENTS

| | | | | |
|---|---|---|---|---|
| 6,146,383 A | * | 11/2000 | Studer | A61B 17/7035 606/256 |
| 8,100,946 B2 | * | 1/2012 | Strausbaugh | A61B 17/7038 606/266 |
| 9,320,546 B2 | | 4/2016 | Keyer | |
| 9,603,632 B1 | | 3/2017 | Gunn | |
| 2004/0147929 A1 | * | 7/2004 | Biedermann | A61B 17/7001 606/266 |
| 2006/0241599 A1 | | 10/2006 | Konieczynski | |
| 2006/0293659 A1 | | 12/2006 | Alvarez | |
| 2007/0016200 A1 | | 1/2007 | Jackson | |
| 2008/0015596 A1 | * | 1/2008 | Whipple | A61B 17/8685 606/86 A |
| 2008/0021474 A1 | | 1/2008 | Bonutti | |
| 2008/0269809 A1 | | 10/2008 | Garamszegi | |
| 2008/0287998 A1 | * | 11/2008 | Doubler | A61B 17/863 606/269 |
| 2010/0036433 A1 | | 2/2010 | Jackson | |
| 2010/0100137 A1 | * | 4/2010 | Justis | A61B 17/7037 606/308 |
| 2011/0106172 A1 | | 5/2011 | Wallenstein | |
| 2012/0041490 A1 | | 2/2012 | Jacob | |
| 2013/0325076 A1 | * | 12/2013 | Palmer | A61B 17/8635 606/318 |

(Continued)

FOREIGN PATENT DOCUMENTS

DE 102016108972 A1 * 11/2017 ......... A61B 17/7032

*Primary Examiner* — Eduardo C Robert
*Assistant Examiner* — Tara Rose E Carter

(57) ABSTRACT

This disclosure presents a polyaxial pedicle screw system. The system may comprise one or more of a screw body, a screw insert, a head component, a bushing, and/or other components. The screw body may have a major diameter. The screw insert may comprise a spherical head having a head diameter. The head component may have an axial bore forming an interior surface which defines a bore diameter of the axial bore. The interior surface may define a narrowest part of the bore diameter of the axial bore at a first end of the head component. The head diameter of the spherical head of the screw insert and/or the major diameter of the screw body may be larger than the narrowest part of bore diameter of the axial bore.

18 Claims, 7 Drawing Sheets

(56) References Cited

U.S. PATENT DOCUMENTS

2013/0345754 A1 12/2013 Doubler
2019/0133660 A1* 5/2019 Lindner ............. A61B 17/7037

* cited by examiner

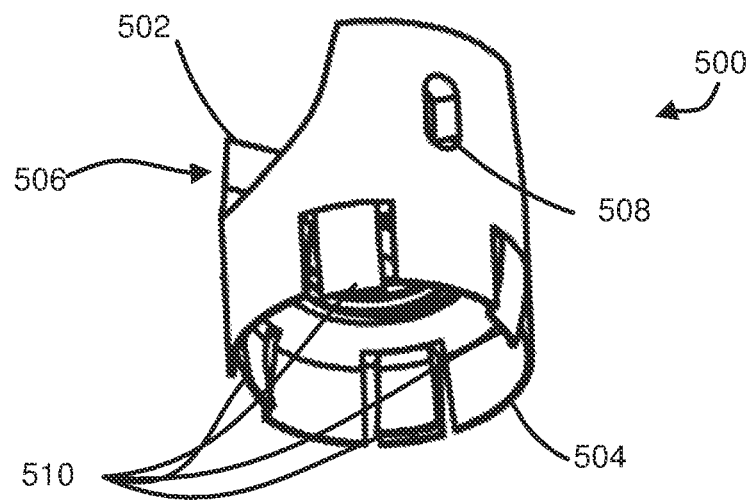
FIG. 9
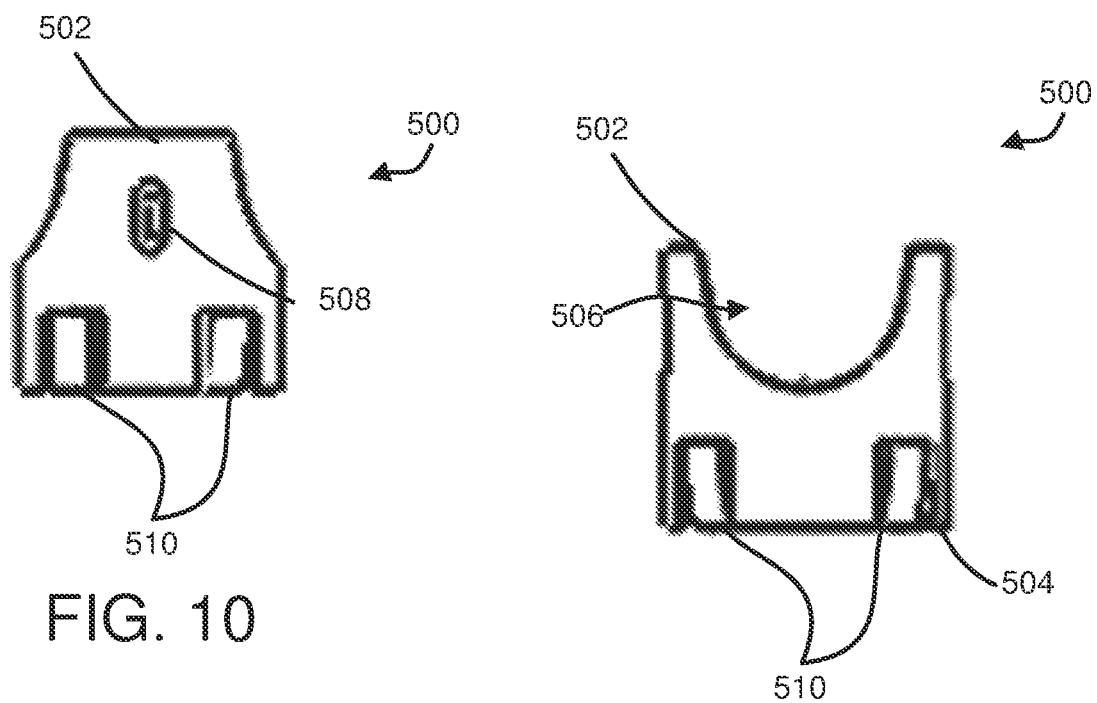
FIG. 10
FIG. 11

POLYAXIAL PEDICLE SCREW SYSTEM

FIELD

This disclosure relates to polyaxial pedicle screws.

BACKGROUND

There are various devices and systems for fixation of bone segments. One type of device is a pedicle screw. The pedicle screw provides a technique of gripping a spinal segment. A conventional pedicle screw is used in conjunction with a rod-receiving device and a rod. The rod-receiving device couples to the pedicle screw and mounts the rod. The rod-receiving device is often referred to as a "tulip."

A pedicle screw system may be polyaxial or monoaxial. A monoaxial pedicle screw system may have the tulip fixedly attached, or formed as part of, the screw itself. The monoaxial pedicle screw system does not permit rotation of the tulip relative the screw. A polyaxial screw system may be formed of multiple parts. Namely, the tulip and pedicle screw may be separate parts that attach together in a manner that allows the tulip to rotate relative the screw.

SUMMARY

One aspect of the disclosure relates to polyaxial pedicle screw system. A conventional polyaxial pedicle screw may be limited in its major diameter (e.g., the outer diameter of the thread(s) on the screw) by virtue of the need to mount the screw to a tulip. For example, a top-loading pedicle screw system may require the pedicle screw to pass through a bore, or passage, of the tulip so that a head of the screw can be seated within the tulip. Thus, the major diameter of the screw may be limited to the diameter of the bore of the tulip so that the threaded part of the screw can pass through to achieve the seating of the head within the tulip. One or more implementations of the system may be configured to solve one or more of the problems associated with conventional pedicle screws.

The system may comprise one or more of a screw body, a screw insert, a head assembly, and/or other components.

The screw body may comprise one or more threads. The one or more threads may define a major diameter of the screw body.

The screw insert may be configured to be inserted into the screw body. The screw insert may comprise a spherical head and/or other components. The spherical head may have a head diameter.

The head assembly may comprise one or more of a head component, a bushing, and/or other components. The head component may be a pedicle screw tulip. The head component may have an axial bore. The axial bore may form an interior surface within the head component which defines a bore diameter of the axial bore. The interior surface may define a narrowest part of the bore diameter of the axial bore at a first end of the head component. The interior surface may confine a volume of space within the head component in which the spherical head of the screw insert may be disposed when assembled. The spherical head may seat against the interior surface at the narrowest part of the bore diameter of the axial bore at the first end of the head component.

The bushing may be configured to be inserted into the axial bore from a second end of the head component opposite the first end. The insertion of the bushing in an assembled mode of the polyaxial pedicle screw system may cause the bushing to frictionally engage between the interior surface of the head component and the spherical head to maintain the seat of the spherical head against the interior surface at the narrowest part of the bore diameter of the axial bore.

With the above components and configuration, the head diameter of the spherical head of the screw insert may be larger than the narrowest part of bore diameter of the axial bore such that the spherical head may be prevented from passing through the narrowest part of the bore diameter of the axial bore. The major diameter of the screw body may be larger than the narrowest part of the bore diameter of the axial bore. Since the major diameter of the screw body may be larger than the narrowest part of the bore diameter of the axial bore, utilization of interchangeable screw bodies having major diameters larger than conventional top-loading screws may be accomplished.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 9 illustrates a view of a bushing of the polyaxial pedicle screw system, in accordance with one or more implementations.

FIG. 10 illustrates another view of the bushing of the polyaxial pedicle screw system, in accordance with one or more implementations.

FIG. 11 illustrates yet another view of the bushing of the polyaxial pedicle screw system, in accordance with one or more implementations.

DETAILED DESCRIPTION

Figure 1:
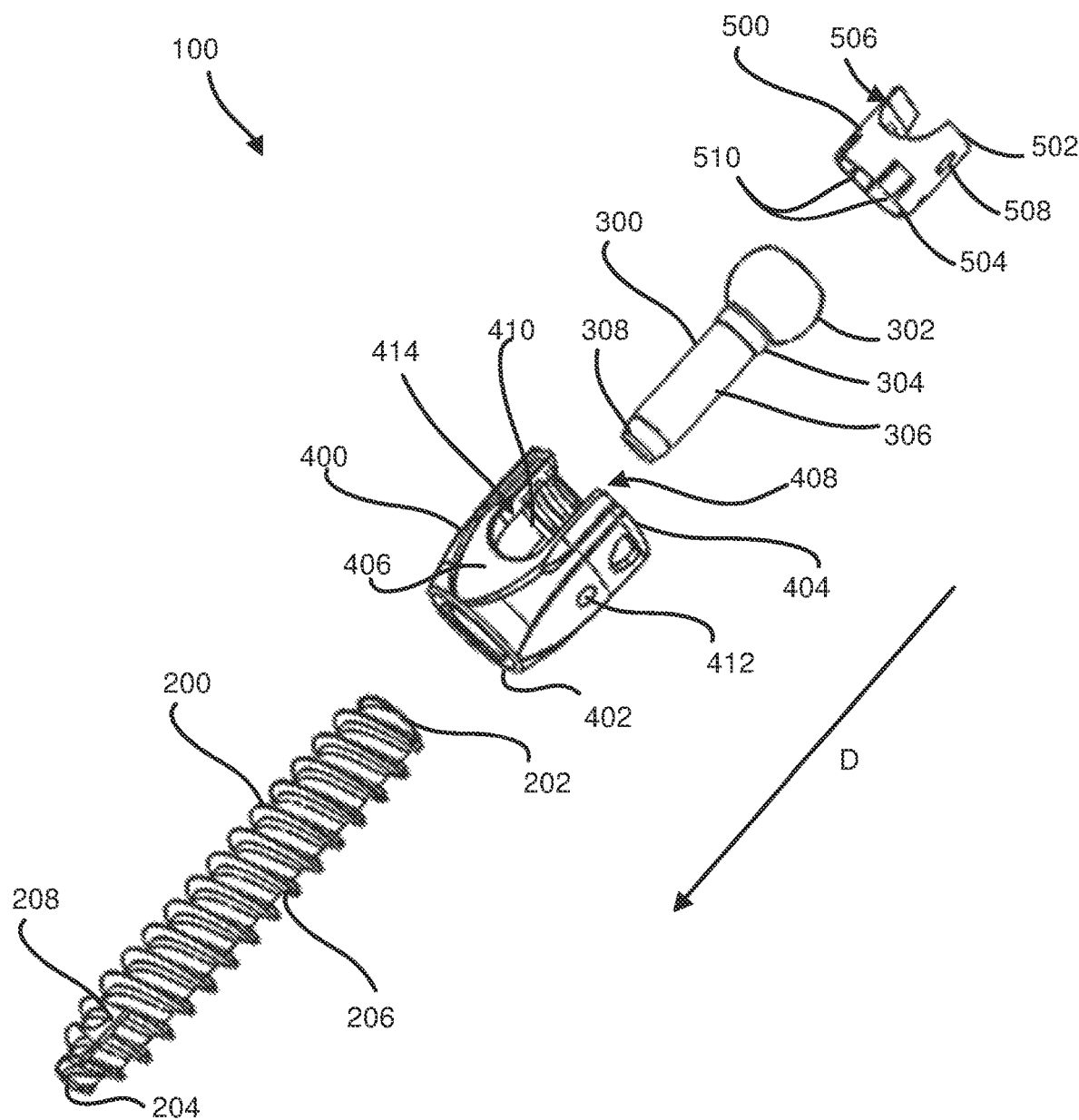
FIG. 1 illustrates a polyaxial pedicle screw system, in accordance with one or more implementations.
Figure 12:
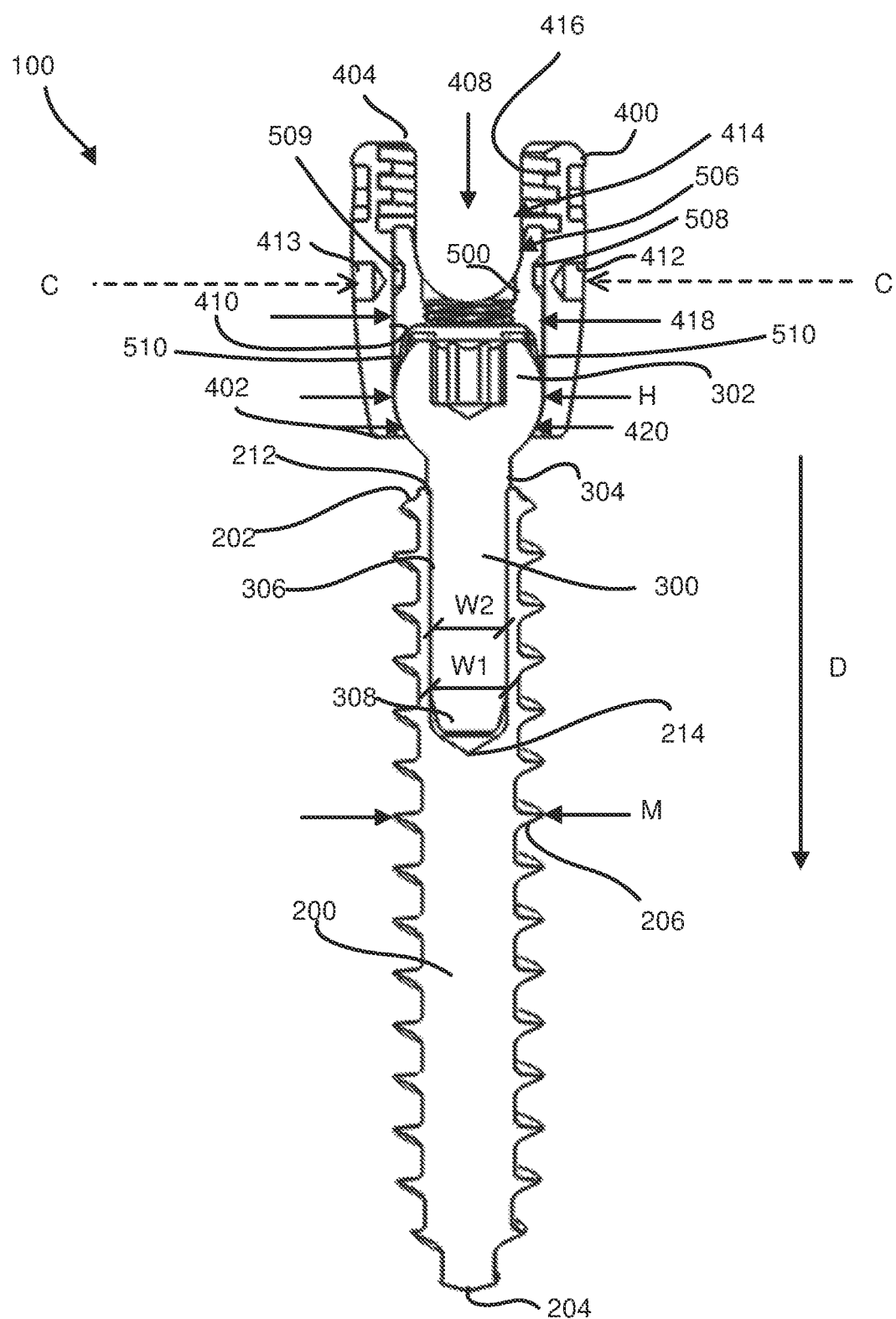
FIG. 12 illustrates a cross-sectional view of the assembled mode of the polyaxial pedicle screw system, in accordance with one or more implementations.
Figure 13:
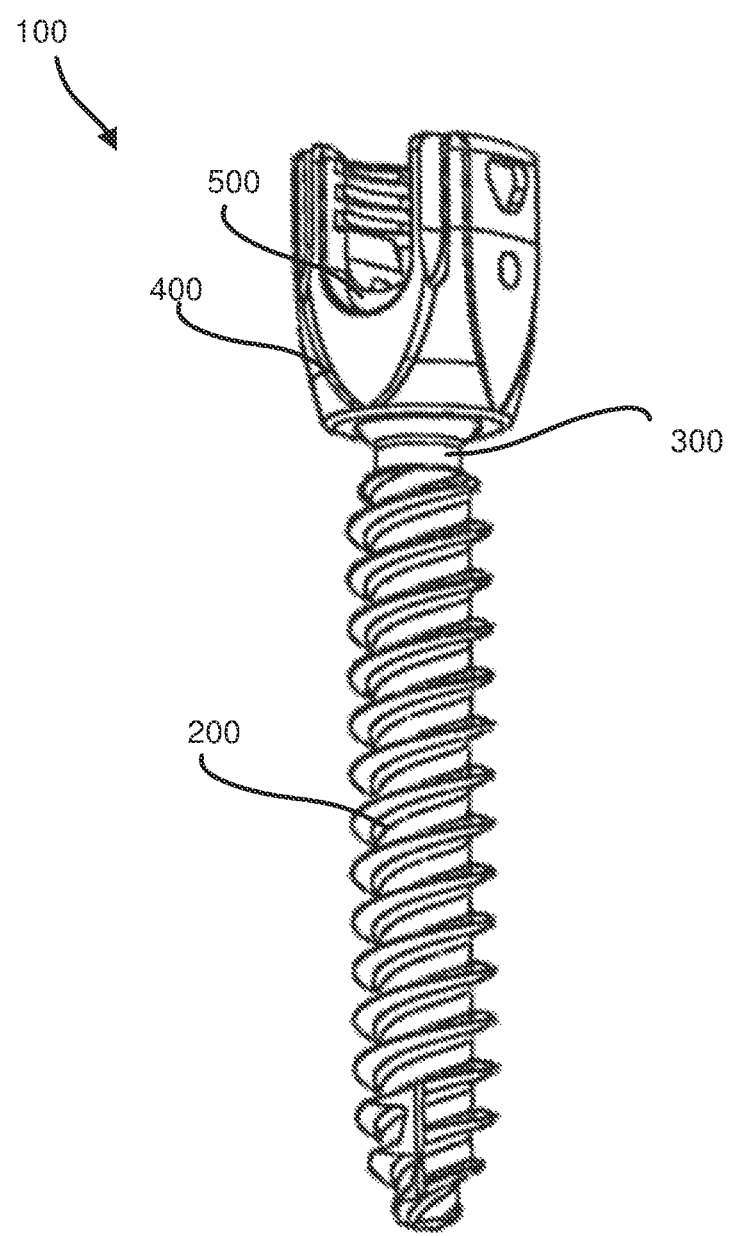
FIG. 13 illustrates an assembled mode of the polyaxial pedicle screw system, in accordance with one or more implementations.

FIG. 1 illustrates a polyaxial pedicle screw system 100, in accordance with one or more implementations. FIG. 1 and accompanying descriptions provide a high-level overview of the system 100, with detailed descriptions of the individual components of system 100 provided in FIGS. 2-11. In addition, assembled views of the system 100 are shown in FIGS. 12 and 13, and described in more detail herein.

The system 100 may comprise one or more of a screw body 200, a screw insert 300, a head assembly, and/or other components. The head assembly may comprise one or more of a head component 400, a bushing 500, and/or other components. One or more components of the system 100 may be assembled through insertion of various components into other ones of the components along an assembly direction "D." The assembly direction D may be in-line with a direction of insertion of the screw body 200 into a pedicle of a vertebrae of a subject (not shown in FIG. 1). One or more components of the system 100 may be formed from one or more materials including one or more of plastic, metal, and/or other materials. By way of non-limiting illustration, one or more components of the system 100 may be formed from titanium.

In FIG. 1, the screw body 200 may comprise one or more of a first end 202, a second end 204 opposite the first end 202, one or more male threads including thread 206, one or more flutes including flute 208, and/or other component. The one or more threads may define a major diameter of the screw body 200 (shown in FIG. 2 and described herein). The second end 204 may comprise a tip of the screw body 200 that may be inserted into a pedicle of a vertebrae of a subject. The assembly direction D may comprise a direction extending from the first end 202 to the second end 204 of screw body 200. In some implementations, the overall length of screw body from first end 202 to second end 204 may be in the range of thirty to 150 millimeters, and/or other lengths.

The screw insert 300 may be configured to be inserted into one or more of the head component 400, the screw body 200, and/or other components of system 100. The screw insert 300 may comprise one or more of a spherical head 302, a shaft, and/or other components. The shaft may be comprise of one or more of a first shaft portion 304, a second shaft portion 306, a third shaft portion 308, and/or other portions. The spherical head 302 may have a head diameter and a driver interface (shown in FIG. 5 and described herein).

The head assembly may comprise one or more of the head component 400, the bushing 500, and/or other components. The head component 400 may be a pedicle screw tulip and/or other device. The head component 400 may have one or more of a first end 402, a second end 404 opposite the first end 402, an exterior surface 406, an interior surface 410, and/or other components. The head component 400 may have an axial bore 408. The axial bore 408 may comprise a passage extending from an opening at the first end 402 to an opening at the second end 404. The axial bore 408 may aligned with a longitudinal axis of the head component 400.

The axial bore 408 may form the interior surface 410 within the head component 400. The interior surface 410 may define a bore diameter of the axial bore 408.

Figure 8:
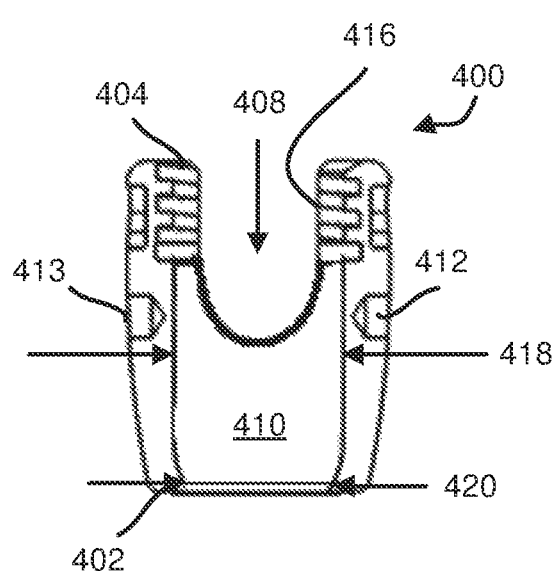
FIG. 8 illustrates cross-sectional view of the head component of the polyaxial pedicle screw system, in accordance with one or more implementations.

The interior surface 410 may define a narrowest part of the bore diameter of the axial bore 408 at the first end 402 of the head component 400 (shown in FIG. 8 and described herein). The interior surface 410 may confine a volume of space within the head component 400. When assembled, the spherical head 302 of the screw insert 300 may be disposed within the volume of space (shown in FIG. 12 and described herein). When assembled, the spherical head 302 may seat against the interior surface 310 at the narrowest part of the bore diameter of the axial bore 408 at the first end 402 of the head component 400.

The bushing 500 may be configured to be inserted into the axial bore 408 along the insertion direction D from the second end 404 of the head component 400. The insertion of the bushing 500 in the assembled mode of the polyaxial pedicle screw system 100 (shown in FIGS. 12 and 13, and described herein) may cause the bushing 500 to frictionally engage between the interior surface 410 of the head component 400 and the spherical head 302 to maintain the seat of the spherical head 302 against the interior surface 410 at the narrowest part of the bore diameter of the axial bore 408.

With the above components and/or configuration, the head diameter of the spherical head 302 of the screw insert 300 may be larger than the narrowest part of bore diameter of the axial bore 408. The spherical head 302 may be prevented from passing through the narrowest part of the bore diameter of the axial bore 408. The major diameter of the screw body 200 may be larger than the narrowest part of the bore diameter of the axial bore 408.

Figure 2:
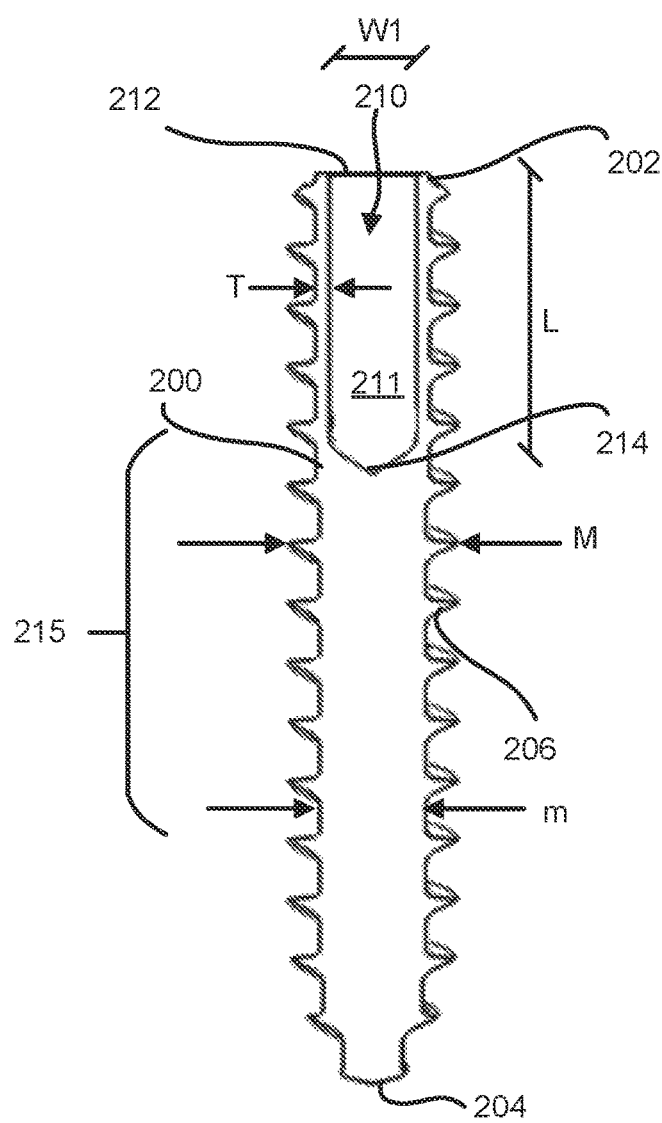
FIG. 2 illustrates a cross-sectional view of a screw body of the polyaxial pedicle screw system, in accordance with one or more implementations.

FIG. 2 illustrates a longitudinal cross-sectional view of the screw body 200, in accordance with one or more implementations. The screw body 200 includes thread 206 which may define one or more of the major diameter "M" of the screw body 200, a minor diameter "m" of the screw body 200, and/or other features.

The screw body 400 may include an internal bore 210. The internal bore 210 may form an opening 212 at the first end 202 of screw body 200. The internal bore 210 may have a terminating end 214. The terminating end 214 may be in a middle portion 215 of screw body 200. The internal bore 210 may form an interior surface 211 within screw body 400. The interior surface 211 may define a passage extending into the screw body 200 that may be aligned with a longitudinal axis of the screw body 400. The interior surface 211 may define a bore diameter of the internal bore 210. The shaft of the screw insert (not shown in FIG. 2) may be inserted into the internal bore 210 of the screw body 200. The length "L1" of the internal bore 210 extending from the opening 212 to the terminating end 214 may be selected based on a length of the shaft of the screw insert. The width "W1" of the internal bore 210 (e.g., the diameter of the bore 210) may be selected based on a width (e.g., diameter) of the shaft of the screw insert. In some implementations, the width W1 of the internal bore 210 may be selected so that a wall thickness "T" of the screw body formed by the internal bore 210 is sufficient as to prevent the screw body 200 from breaking under certain torques.

Figure 3:
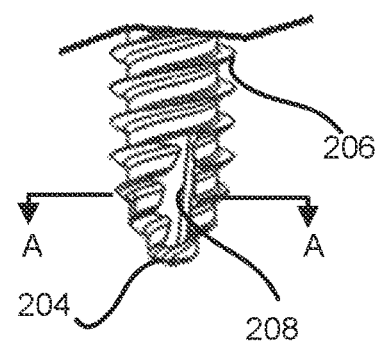
FIG. 3 shows a close-up view of an end of a screw body of the polyaxial pedicle screw system, in accordance with one or more implementations.
Figure 4:
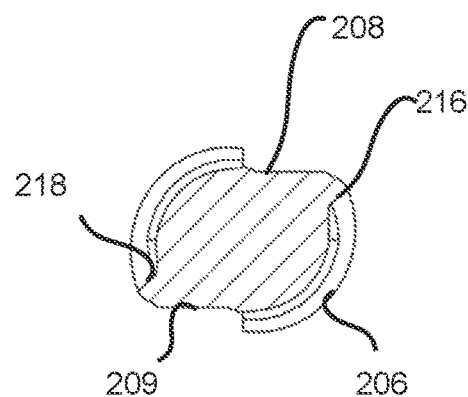
FIG. 4 illustrates a cross-sectional view of an end of a screw body of the polyaxial pedicle screw system, in accordance with one or more implementations.

FIG. 3 shows a close-up view of second end 204 of the screw body 200. The screw body 200 may include one or more flutes including flute 208. The one or more flutes may be machined into the send end 204 of the screw body 200 to provide one or more cutting edges. The one or more flutes may make the screw body 200 self-tapping. FIG. 4 illustrates a cross-sectional view of the second end 204 of the screw body 200 as seen from section AA of FIG. 3. In FIG. 4, the flute 208 and a second flute 209 opposite the flute 208 are shown. The flute 208 may provide a first cutting edge 216. The second flute 209 may provide a second cutting edge 218.

Figure 5:
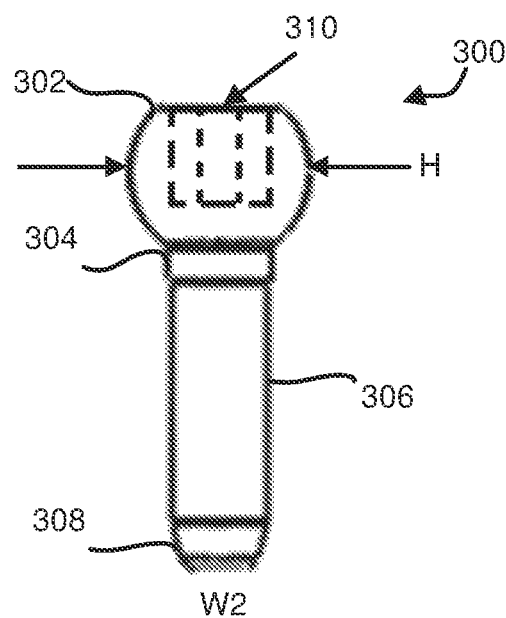
FIG. 5 illustrates a screw insert of the polyaxial pedicle screw system, in accordance with one or more implementations.

FIG. 5 illustrates a view of the screw insert 300. The screw insert 300 may comprise one or more of spherical head 302, first shaft portion 304, second shaft portion 306, third shaft portion 308, driver interface 310 (shown by dashed lines), and/or other components. The third shaft portion 308 may comprise a tapered end of screw insert 300. The first shaft proton 304 may be wider than the second shaft portion 306. The first shaft portion 304 may form a collar. The width of the first shaft portion 304 may be wider than the opening 212 of the internal bore 210 of the shaft body 200 (shown in FIG. 12 and described herein). The second shaft portion 306 and the third shaft portion 308 may inserted into the internal bore 210 of the screw body 200 (shown in FIG. 12 and described herein). When inserted, the collar formed by first shaft portion 304 may interface around the opening 212 of the internal bore at the first end 202 of the shaft body 200.

The second shaft portion 306 may have a width W2 (e.g., the diameter of second shaft portion 306). In some implementations, the width W2 of second shaft portion 306 may be formed larger than width W1 of the internal bore 210 of the shaft body 200 (FIG. 2) so as to achieve a press-fit (or friction fit) engagement of screw insert 300 into the internal bore 210 of the shaft body 200. In some implementations, W2 may be a value within the range of three to six millimeters, and/or other values.

The head diameter "H" of the spherical head 302 may be measured as the maximum diameter of the spherical head 302. The spherical head 302 may be truncated at the driver interface 310 as shown so that the spherical head 302 may not form a complete sphere.

The driver interface 310 may be configured to receive a driving tool for advancing or removing the assembled system 100 into a bone segment. By way of non-limiting illustration, the drive interface 310 may comprise one or more of a hex driver interface, a Phillips head interface, a flathead interface, and/or other driver interface configured to receive a driving tool for advancing or removing the system 100 into bone.

Figure 6:
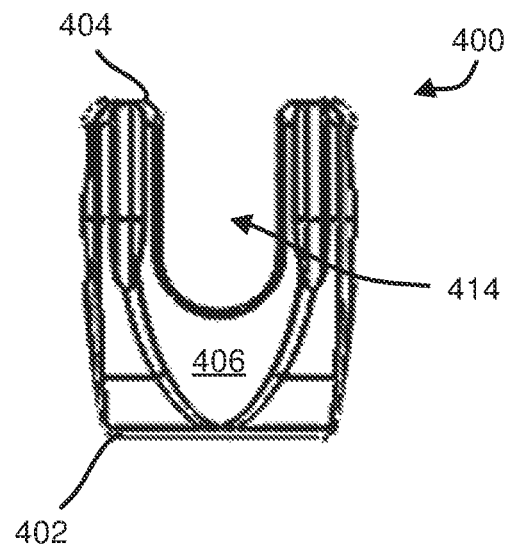
FIG. 6 illustrates a view of a head component of the polyaxial pedicle screw system, in accordance with one or more implementations.
Figure 7:
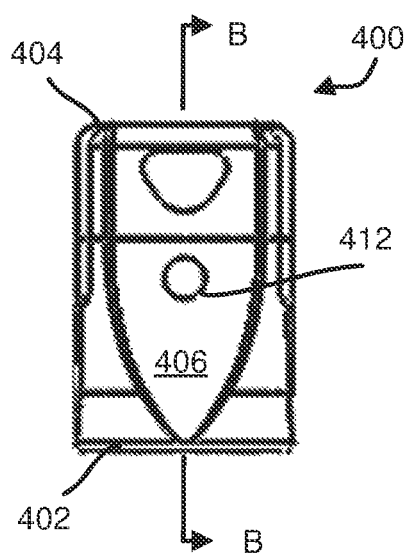
FIG. 7 illustrates another view of the head component of the polyaxial pedicle screw system, in accordance with one or more implementations.

FIG. 6 illustrates a view of the head component 400. The head component 400 may comprise a pedicle screw tulip. The head component 400 may be of a one-piece construction. That is, no other components may be required to form the head component 400. By way of non-limiting illustration, head component 400 may be milled from a single piece of material. As shown in FIG. 6, head component 400 may include a U-shaped rod-receiving channel 414. The channel 414 may be used for coupling a rod (not shown in FIG. 6) to head component 400 during operative use in fixing bone segments together. FIG. 7 illustrates another view of the head component 400 of the polyaxial pedicle screw system 100.

FIG. 8 illustrates cross-sectional view of the head component 400 as seen from section BB of FIG. 7. The head component 400 may include one or more locking components including first locking component 412 and/or second locking component 413. The first locking component 412 may be disposed opposite second locking component 413. The first locking component 412 and/or second locking component 413 may be configured to align with complementary locking components of the bushing 500 (shown in FIG. 9 and FIG. 12, described herein). Once aligned, a crimping tool (not shown) may be inserted into the first locking component 412 and/or second locking component 413 and the tool compressed. The compression may cause material of head component 400 forming the first locking component 412 and/or second locking component 413 to deform inward (e.g., into axial bore 408). The deformed material may protrude into the aligned complementary locking components of the bushing 500, causing the head component 400 and bushing 500 to become locked together. In some implementations, the one or more locking components of head component 400 and the one or more complementary locking components of the bushing 500 may comprise small cavities.

Shown more clearly in FIG. 8 is the axial bore 408. The axial bore 408 may comprise a passage extending from an opening at the second end 404 to an opening at the first end 402. The axial bore 408 may form the interior surface 410 within the head component 400. The interior surface 410 may define a bore diameter 418 of the axial bore 408. The interior surface 410 may further define a narrowest part 420 of the bore diameter 418 of the axial bore 408 at the first end 402 of the head component 400. In some implementations, the narrowest part 420 of the bore diameter 418 of the axial bore 408 may be formed by tapering the bore diameter 418 at the first end 402 of the head component 400. In some implementations, the tapering may start 1 to 2 millimeters from the opening at the first end 402. In some implementations, the narrowest part 420 of the bore diameter 418 of the axial bore 408 may be formed by an inwardly projecting flange, or ridge, disposed at the opening of the axial bore 408 at the first end 402.

In some implementations, bore diameter 418 may be uniform in diameter from the opening at the second end 404 to the narrowest part 420. In some implementations, one or more female threads 416 may be formed into the interior surface 410 at the second end 404. The one or more female threads 416 may be configured to receive a cap (not shown in FIG. 8) for securing a rod (not shown) into the U-shaped channel 414.

The narrowest part 420 may have a diameter that may be smaller than the head diameter H of the spherical head (FIG. 5). The bore diameter 418 may be equal to and/or larger than the head diameter H of the spherical head (FIG. 5). The axial bore 408 may permit insertion of the screw insert 300 into the axial bore 408 until the spherical head 302 seats at the narrowest part 420 of the bore diameter 418 of the axial bore 408 at the first end 402 of the head component 400.

FIG. 9 illustrates a view of bushing 500 configured to be inserted into the axial bore 408 of the head component 400. The bushing 500 may be a cylindrical lining used to frictionally engage within the axial bore 408 of the head component 400 to maintain a seat of the spherical head 302 of the screw insert 300 in head component 400. The bushing 500 may include one or more of a first end 502, a second end 504 opposite the first send 502, a U-shaped rod-receiving channel 506, one or more complementary locking components including third locking component 508 and/or a fourth locking component 509 opposite the third locking component 508 (not shown in FIG. 9), one or more shims 510, and/or other components. When assembled, the channel 506 may be aligned with channel 414 of head component 400. The channel 506 may accommodate the coupling of a rod to head component 400 via the channel 414 of head component 400.

The one or more shims 510 may comprise articulatable components disposed at the second end 504 of the bushing 500 configured to frictionally engage between the interior surface 410 of the head component 400 and the spherical head 302 of the screw insert 300 when assembled (shown in FIG. 12 and described herein). FIGS. 10 and 11 shows other views the bushing 500.

FIG. 12 illustrates a cross-sectional view of the assembled mode of the polyaxial pedicle screw system 100, in accordance with one or more implementations. As shown, the screw insert 300 may be inserted into the axial bore 408 of head component 400 until spherical head 302 seats against interior surface 410 at the narrowest part 420 of the bore diameter of the axial bore 408. The bushing 500 may be inserted from the second end 404 of the head component 400. The one or more shims 510 may wedge between the spherical head 302 and the interior surface 410 at the narrowest part 420 of the bore diameter of the axial bore 408 to maintain the seat of the spherical head 302. The U-shaped channel 414 of the head component 400 may be aligned with U-shaped channel 506 of the bushing 500 to accommodate a rod.

The spherical head 302 may be prevented from passing through the narrowest part 420 causing the spherical head 302 to seat against the interior surface 410 at the narrowest part 420 of the bore diameter of the axial bore 408. In some implementations, the head diameter H may be 8 millimeters or larger. In some implementations, the narrowest part 420 of the bore diameter of the axial bore 408 may be less than 8 millimeters. In some implementations, the major diameter M may be in the range of 8 to 11 millimeters, inclusive. In some implementations, the major diameter M may be larger than 11 millimeters.

The first locking component 412 and second locking component 413 of the head component 400 may be aligned with the complementary third locking component 508 and fourth locking component 509 of bushing 500. Once aligned, a crimping tool (not shown) may be inserted into the first locking component 412 and/or second locking component 413 and a compressive force "C" may be applied inward (shown by dashed lines). The compression may cause material of head component 400 inside the first locking component 412 and/or second locking component 413 to deform inward (e.g., into axial bore 408). The deformed material may protrude into the aligned complementary third locking component 508 and fourth locking component 509 of bushing 500, causing the head component 400 and bushing 500 to become locked together, thereby locking the spherical head 302 in it's seating.

The screw insert 300 may be inserted into the internal bore 210 of the shaft body 200. The second shaft portion 306 and the third shaft portion 308 may inserted into the internal bore 210 of the screw body 200. The third shaft portion 308 may be inserted first and advanced toward the terminating end 214 of the bore 210. The width (e.g., diameter) of the first shaft portion 304 may be wider than the opening 212 of the internal bore 210 of the shaft body 200. When inserted, the collar formed by first shaft portion 304 may interface around the opening 212 of the internal bore at the first end 202 of the shaft body 200. In some implementations, the screw insert 300 may be fixedly attached to the screw body 200 by one or more of adhesive, welding, threaded engagement, and/or other techniques. By way of non-limiting illustration, the first shaft portion 304 may we be welded, or adhesive applied, at the interface with the opening 212 of the internal bore at the first end 202 of the shaft body 200. In some implementations, the second shaft portion 306 may include male threads and an interior surface formed by the internal bore of the shaft body 200 may include female threads (not shown).

FIG. 13 illustrates an assembled mode of the polyaxial pedicle screw system 100 including the screw body 200, screw insert 300, head component 400, and bushing 500.

Figure 14:
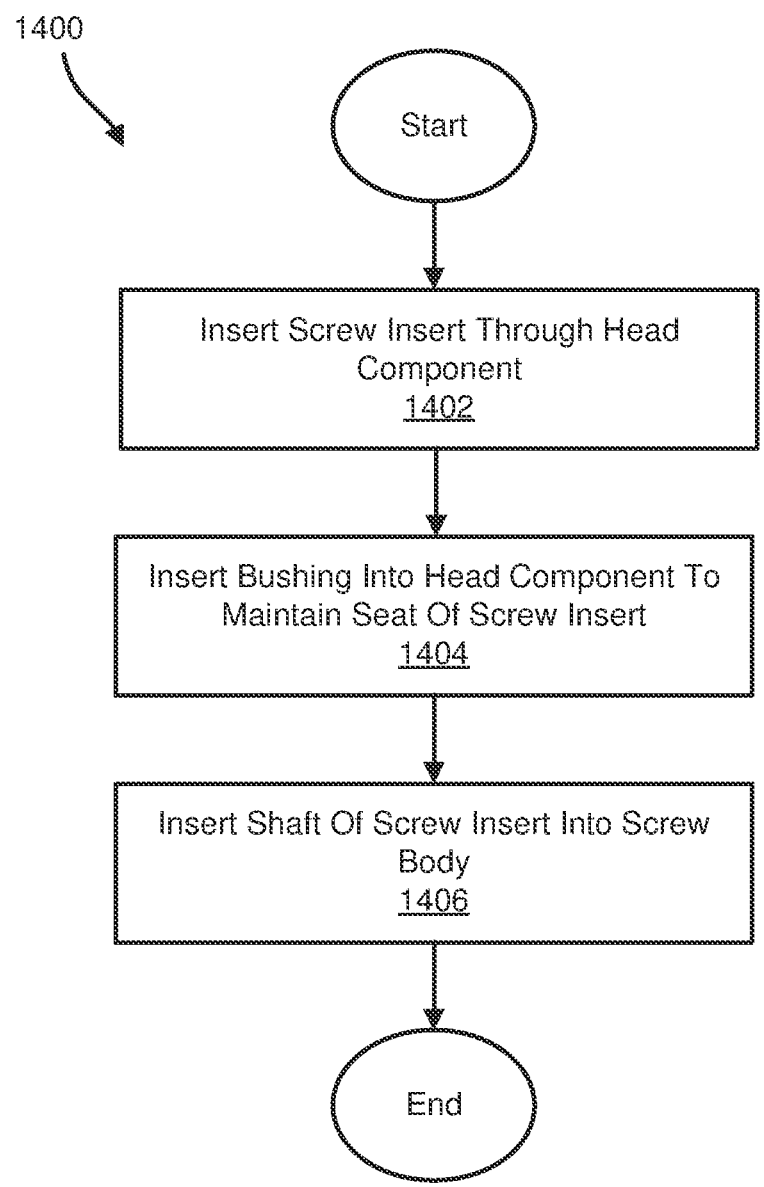
FIG. 14 illustrates a method of assembling a polyaxial pedicle screw system, in accordance with one or more implementations.

FIG. 14 illustrates a method 1400 of assembling a polyaxial pedicle screw system. The operations of method 1400 presented below are intended to be illustrative. In some implementations, method 1400 may be accomplished with one or more additional operations not described, and/or without one or more of the operations discussed. Additionally, the order in which the operations of method 1400 are illustrated in FIG. 14 and described below is not intended to be limiting. In some implementations, method 1400 may be implemented using a polyaxial pedicle screw system the same as or similar to polyaxial pedicle screw system 100 (shown in FIGS. 1-13 and described herein).

At an operation 1402, a screw insert may be inserted along an insertion direction through a head component. The screw insert may include a spherical head and a shaft. The spherical head may have a head diameter. The head component may have an axial bore. The axial bore may form an interior surface within the head component which defines a bore diameter of the axial bore. The interior surface may define a narrowest part of the bore diameter of the axial bore at a first end of the head component. The interior surface may confine a volume of space within the head component in which the spherical head of the screw insert may be disposed. The head diameter may be larger than the narrowest part of bore diameter of the axial bore such that the spherical head may be prevented from passing through the narrowest part of the bore diameter of the axial bore causing the spherical head to seat against the interior surface at the narrowest part of the bore diameter of the axial bore at the first end of the head component. In some implementations, operation 1402 may be performed using a screw insert and a head component the same as or similar to screw insert 300 and head component 400, respectively (shown in FIG. 1 and described herein).

At an operation 1404, a bushing may be inserted along the insertion direction into the axial bore from a second end of the head component. The insertion of the bushing may cause the bushing to frictionally engage between the interior surface and the spherical head to maintain the seat of the spherical head against the interior surface at the narrowest part of the bore diameter of the axial bore. In some implementations, operation 1404 may be performed using a bushing the same as or similar to bushing 500 (shown in FIG. 1 and described herein).

At an operation 1406, the shaft of the screw insert may be inserted along the insertion direction into a screw body. The screw body may have one or more threads. The one or more threads may define a major diameter of the screw body. The major diameter of the screw body may be larger than the narrowest part of the bore diameter of the axial bore. In some implementations, operation 1406 may be performed using a screw body the same as or similar to screw body 200 (shown in FIG. 1 and described herein).

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A polyaxial pedicle screw system, the system comprising:
a screw body, the screw body comprising:
a thread defining a major diameter of the screw body and extending to a first end of the screw body; and
an internal bore forming an opening at the first end of the screw body;
a screw insert configured to be inserted into the screw body, the screw insert comprising a tapered end opposite a spherical head, the spherical head having a head diameter and the tapered end being configured to be inserted into the screw body and secured via a press fit such that the screw insert is secured within the screw body via the press fit; and
a head assembly, the head assembly comprising:
a head component having an axial bore, the axial bore forming an interior surface within the head component which defines a bore diameter of the axial bore, the interior surface defining a narrowest part of the bore diameter of the axial bore at a first end of the head component, the interior surface confining a volume of space within the head component in which the spherical head of the screw insert is disposed;
wherein:
the head diameter is larger than the narrowest part of bore diameter of the axial bore such that the spherical head is prevented from passing through the narrowest part of the bore diameter of the axial bore;
the major diameter of the screw body is larger than the narrowest part of the bore diameter of the axial bore, and
an end diameter of the first end of the screw body, where the internal bore forms the opening at the first end, is defined by the thread that extends to the first end of the screw body such that the end diameter is the same as the major diameter and the first end of the screw body does not include a spherical component that requires a diameter defined by the head component.

2. The system of claim 1, wherein the head assembly further comprises:
a bushing configured to be inserted into the axial bore from a second end of the head component, the insertion of the bushing causing the bushing to frictionally engage between the interior surface and the spherical head to maintain the seat of the spherical head against the interior surface at the narrowest part of the bore diameter of the axial bore.

3. The system of claim 1, wherein the head component is a pedicle screw tulip.

4. The system of claim 3, wherein the pedicle screw tulip is of one-piece construction.

5. The system of claim 1, wherein the head diameter is a maximum diameter of the spherical head.

6. The system of claim 1, wherein the internal bore has an opening at an end of screw body that terminates at a middle portion of the screw body.

7. The system of claim 6, wherein the screw insert further includes:
a first shaft portion forming a collar;
a second shaft portion; and
a third shaft portion comprising the tapered end.

8. The system of claim 7, wherein the second shaft portion and the third shaft portion are inserted in to the internal bore of the screw body, and wherein the first shaft portion forming the collar is wider than the opening of the internal bore.

9. The system of claim 1, wherein the screw insert further includes a driver interface in the spherical head.

10. The system of claim 1, wherein the major diameter is in the range of 8 to 11 millimeters, inclusive.

11. The system of claim 10, wherein the narrowest part of the bore diameter of the axial bore is less than 8 millimeters.

12. The system of claim 11, wherein the head diameter is 8 millimeters or larger.

13. A method of assembling a polyaxial medical screw, the method comprising:
inserting, along an insertion direction, a screw insert through a head component, wherein the screw insert includes a spherical head and a shaft, the spherical head having a head diameter, wherein the head component has an axial bore forming an interior surface within the head component, the interior surface defining a bore diameter of the axial bore, the interior surface defining a narrowest part of the bore diameter of the axial bore at a first end of the head component, wherein the head diameter is larger than the narrowest part of bore diameter of the axial bore such that the spherical head is prevented from passing through the narrowest part of the bore diameter of the axial bore causing the spherical head to seat against the interior surface at the narrowest part of the bore diameter of the axial bore at the first end of the head component;
inserting, along the insertion direction, a bushing into the axial bore from a second end of the head component, the insertion of the bushing causing the bushing to frictionally engage between the interior surface and the spherical head to maintain the seat of the spherical head against the interior surface at the narrowest part of the bore diameter of the axial bore; and
press fitting, along the insertion direction, the shaft of the screw insert into a screw body such that the shaft of the screw insert is secured within the screw body via the press fit, wherein the shaft of the screw insert has a tapered end opposite the spherical head and wherein screw body has one or more threads and an internal bore forming an opening at a first end of the screw body, the one or more threads defining a major diameter of the screw body and extending to the first end of the screw body, wherein the major diameter of the screw body is larger than the narrowest part of the bore diameter of the axial bore and an end diameter of the first end of the screw body is defined by the one or more threads that extend to the first end of the screw body such that the end diameter is the same as the major diameter of the screw body and the first end of the screw body does not include a spherical component that requires a diameter defined by the head component.

14. The method of claim 13, wherein the internal bore terminates at a middle portion of the screw body.

15. The method of claim 13, wherein the head component is a pedicle screw tulip.

16. The method of claim 13, wherein the major diameter is in the range of 8 to 11 millimeters, inclusive.

17. The method of claim 16, wherein the narrowest part of the bore diameter of the axial bore is less than 8 millimeters.

18. The method of claim 17, wherein the head diameter is 8 millimeters or larger.

* * * * *